United States Patent
Yoshida et al.

(10) Patent No.: US 6,340,757 B1
(45) Date of Patent: Jan. 22, 2002

(54) 6-(1-FLUOROALKYL)-4-PYRIMIDONES AND PROCESSES FOR PRODUCING THE SAME

(75) Inventors: Hiroshi Yoshida; Kiyoshi Ohmori; Kensaku Fuse; Kazuhiro Morita; Yoshitaka Onduka; Naoyuki Yokota, all of Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/623,249
(22) PCT Filed: Mar. 3, 1999
(86) PCT No.: PCT/JP99/01009
  § 371 Date: Aug. 3, 2000
  § 102(e) Date: Aug. 3, 2000
(87) PCT Pub. No.: WO99/44997
  PCT Pub. Date: Sep. 10, 1999

(30) Foreign Application Priority Data

Mar. 6, 1998 (JP) .......................... 10-055174
May 25, 1998 (JP) .......................... 10-142662

(51) Int. Cl.⁷ .................. C07D 239/02; A01N 43/60
(52) U.S. Cl. ............................ 544/319; 504/136
(58) Field of Search ................... 544/319; 504/136

(56) References Cited

U.S. PATENT DOCUMENTS 5,498,612 A  3/1996  Obata et al. ............... 514/256
5,532,208 A * 7/1996  Nagano et al. ............. 504/239

FOREIGN PATENT DOCUMENTS

JP   5-230036    9/1993
WO   WO96/22980  8/1996

* cited by examiner

Primary Examiner—John M. Ford
Assistant Examiner—Tamthom N. Truong
(74) Attorney, Agent, or Firm—Jordan and Hamburg LLP

(57) ABSTRACT

The present invention is to provide a novel 6-(1-fluoroalkyl)-4-pyrimidone represented by the following formula (1):

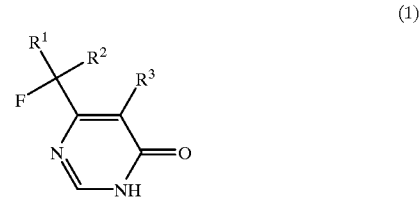

(1)

wherein $R^1$ represents an alkyl group; $R^2$ represents a hydrogen atom or an alkyl group; and $R^3$ represents a hydrogen atom, an alkyl group or a chlorine atom, which is important for a synthetic intermediate for aminopyrimidine derivatives which are useful as acaricides, fungicides or nematocides, and processes for producing the same.

12 Claims, No Drawings

6-(1-FLUOROALKYL)-4-PYRIMIDONES AND PROCESSES FOR PRODUCING THE SAME

BACKGROUND OF THE INVENTION

This invention relates to a 6-(1-fluoroalkyl)-4-pyrimidone and processes for producing the same, more specifically, to a novel 6-(1-fluoroalkyl)-4-pyrimidone which is important as a synthetic intermediate of aminopyrimidine derivatives which are useful as acaricides, fungicides and nematocides, and processes for producing the same.

FIELD OF THE INVENTION

Aminopyrimidine derivatives useful as insecticides, acaricides, fungicides or nematocides have been described, for example, in Japanese Provisional Patent Publications No. 230036/1993, No. 25187/1994, No. 116247/1994, No. 247939/1994, No. 258223/1995, etc. However, the synthetic intermediates of the present invention have not yet been known as synthetic intermediates for the aminopyrimidine derivatives, and thus, the process for producing the same has not yet been known.

The present invention provides a novel 6-(1-fluoroalkyl)-4-pyrimidone which is important as a synthetic intermediate and a process for producing the same.

The present invention solves the above-mentioned problems, and as a result, 6-(1-fluoroalkyl)-4-pyrimidone which is a novel compound can be an important intermediate of the above-mentioned useful aminopyrimidine derivatives. A process for producing 6-(1-fluoroalkyl)-4-pyrimidone is also set forth.

SUMMARY OF THE INVENTION

The first aspect of the present invention relates to 6-(1-fluoroalkyl)-4-pyrimidones represented by the following formula (1):

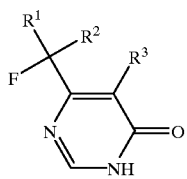

wherein $R^1$ represents an alkyl group; $R^2$ represents a hydrogen atom or an alkyl group; and $R^3$ represents a hydrogen atom, an alkyl group or a chlorine atom.

The second aspect of the invention relates to a process for producing 6-(1-fluoroalkyl)-4-pyrimidones represented by the following formula (1-A):

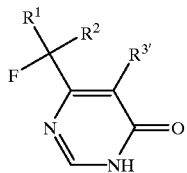

wherein $R^1$ and $R^2$ have the same meanings as defined above; and $R^{3'}$ represents a hydrogen atom or an alkyl group, which comprises allowing a 4-fluoro-3-oxocarboxylate represented by the following formula (2):

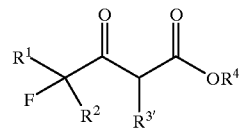

wherein $R^1$, $R^2$ and $R^{3'}$ have the same meanings as defined above; and
$R^4$ represents an alkyl group,
to react with formamidine in the presence of a base.

The third aspect of the invention relates to a process for producing 5-chloro-6-(1-fluoroalkyl)-4-pyrimidones represented by the following formula (1-B):

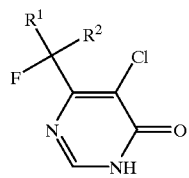

wherein $R^1$ and $R^2$ have the same meanings as defined above, which comprises subjecting 6-(1-fluoroalkyl)-4-pyrimidone represented by the following formula (1-A'):

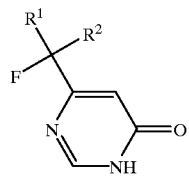

wherein $R^1$ and $R^2$ have the same meanings as defined above, to chlorination reaction with a chlorinating agent.

DETAILED DESCRIPTION OF THE INVENTION

In the following, the present invention will be explained in more detail.

$R^1$ to $R^4$ in the above-mentioned formula (1) are as mentioned below.

$R^1$ to $R^4$ in 6-(1-fluoroalkyl)-4-pyrimidone (Compound (1)) which is represented by the above-mentioned formula (1) which is a compound of the present invention and in 4-fluoro-3-oxocarboxylate (Compound (2)) represented by formula (2) which is a starting material, are as mentioned below.

$R^1$ is a straight or branched alkyl group.

The alkyl group in $R^1$ has 1 to 10 carbon atoms, preferably 1 to 4.

$R^2$ is a hydrogen atom, or a straight or branched alkyl group.

$R^3$ is a hydrogen atom, a straight or branched alkyl group or a chlorine atom.

$R^{3'}$ is a hydrogen atom or a straight or branched alkyl group.

The alkyl group in $R^2$, $R^3$ and $R^{3'}$ has 1 to 10 carbon atoms, preferably 1 to 4, and more preferably a methyl group.

$R^4$ is a straight or branched alkyl group.

The alkyl group in $R^4$ has 1 to 10 carbon atoms, preferably 1 to 4.

The compound (1) of the present invention is exemplified below.

6-(1-Fluoroethyl)-4-pyrimidone,
6-(1-Fluoro-1-methylethyl)-4-pyrimidone,
6-(1-Fluoropropyl)-4-pyrimidone,
6-(1-Fluoro-1-methylpropyl)-4-pyrimidone,
6-(1-Fluorobutyl)-4-pyrimidone,
6-(1-Fluoro-1-methylbutyl)-4-pyrimidone,
6-(1-Fluoropentyl)-4-pyrimidone,
6-(1-Fluoro-1-methylpentyl)-4-pyrimidone,
6-(1-Fluoroethyl)-5-methyl-4-pyrimidone,
6-(1-Fluoro-1-methylethyl)-5-methyl-4-pyrimidone,
6-(1-Fluoropropyl)-5-methyl-4-pyrimidone,
6-(1-Fluoro-1-methylpropyl)-5-methyl-4-pyrimidone,
6-(1-Fluorobutyl)-5-methyl-4-pyrimidone,
6-(1-Fluoro-1-methylbutyl)-5-methyl-4-pyrimidone,
6-(1-Fluoropentyl)-5-methyl-4-pyrimidone,
6-(1-Fluoro-1-methylpentyl)-5-methyl-4-pyrimidone,
5-Chloro-6-(1-fluoroethyl)-4-pyrimidone,
5-Chloro-6-(1-fluoro-1-methylethyl)-4-pyrimidone,
5-Chloro-6-(1-fluoropropyl)-4-pyrimidone,
5-Chloro-6-(1-fluoro-1-methylpropyl)-4-pyrimidone,
5-Chloro-6-(1-fluorobutyl)-4-pyrimidone,
5-Chloro-6-(1-fluoro-1-methylbutyl)-4-pyrimidone,
5-Chloro-6-(1-fluoropentyl)-4-pyrimidone,
5-Chloro-6-(1-fluoro-1-methylpentyl)-4-pyrimidone, and the like.

The compound (2) which is a starting material to be used in the present invention can be easily obtained from a carboxylate

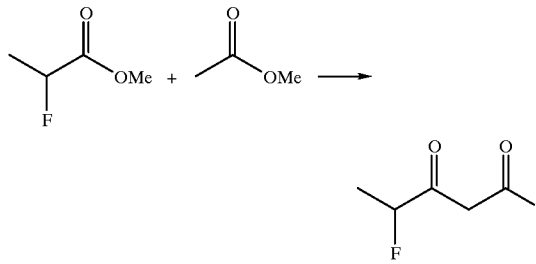

Formamidine to be used in the present invention may be used in the form of a salt, for example, an acetate, a hydrochloride, a sulfate, etc., of formamidine.

An amount of the formamidine salt to be used is preferably 1-fold mole or more, more preferably 1- to 3-fold mole based on the amount of the compound (2).

The base to be used is preferably an alkali metal alkoxide such as sodium methoxide, sodium ethoxide, sodium butoxide, potassium t-butoxide, etc.

An amount of the base to be used is preferably 1-fold mole or more, more preferably 1- to 3-fold mole based on the amount of the formamidine salt.

Synthesis of the compound (1-A) may be carried out without using any solvent, and when a solvent is used, it is not particularly limited so long as it does not participate in the present reaction. There may be mentioned, for example, an alcohol such as methanol, ethanol, 1-propanol, 2-propanol, 1-butanol, etc., an amide such as N,N-dimethylformamide, N,N-dimethylacetamide, etc., an ether such as tetrahydrofuran, dimethoxyethane, etc. Also, these solvents may be used singly or in admixture.

An amount of the solvent to be used is preferably 1- to 50-fold volume, more preferably 2- to 30-fold volume based on the amount of the compound (2).

In the synthesis of the compound (1-A), a reaction temperature to be employed is preferably −10 to 100° C., more preferably 0 to 70° C.

A reaction time in the synthesis of the compound (1-A) may vary depending on the concentration, temperature and amounts to be used, but generally is 0.5 to 15 hours.

The chlorinating agent to be used in the present invention is preferably a chlorine and sulfuryl chloride.

An amount of the chlorinating agent to be used in the present invention is preferably 0.9-fold mole or more, more preferably 0.9 to 4.0-fold mole based on the amount of the compound (1-A′).

In the synthesis of the compound (1-B), a solvent may be used or may not be used, and when a solvent is used, it is not particularly limited so long as it does not participate in the present reaction. For example, an aliphatic halogenated hydrocarbon such as dichloromethane, chloroform, dichloroethane, etc., an aromatic halogenated hydrocarbon such as chlorobenzene, etc., an amide such as N,N-dimethylformamide, N,N-dimethylacetamide, etc., an ether such as diethyl ether, tetrahydrofuran, dimethoxyethane, etc. may be used singly or in admixture.

An amount of the solvent to be used is preferably 0- to 50-fold volume, more preferably 2- to 30-fold volume based on the amount of the compound (1-A′).

In the synthesis of the compound (1-B) of the present invention, a reaction temperature to be employed is preferably −10 to 100° C., more preferably −5 to 70° C.

A reaction time in the synthesis of the compound (1-B) of the present invention may vary depending on the concentration, temperature and amounts to be used, but is generally 0.5 to 10 hours.

The compound (1) of the present invention prepared as mentioned above may be subjected to post-treatments such as washing, extraction, concentration, etc., after completion of the reaction, and may be purified by conventionally known means such as recrystallization, various kinds of chromatography, etc., depending on necessity.

An aminopyrimidine derivative useful as insecticide, acaricide, fungicide, or nematocide can be obtained from the thus obtained compound (1).

For example, as shown below, by chlorinating the 4-position of 5-chloro-6-(1-fluoroethyl)-4-pyrimidone (compound (1-B)) which is one embodiment of the compound (1), 4,5-dichloro-6-(1-fluoroethyl)pyrimidine can be obtained which is an important synthetic intermediate of useful aminopyrimidine derivatives.

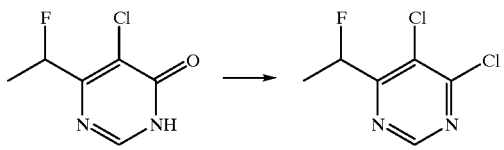

EXAMPLES

In the following, the present invention will be explained by referring to Examples and Reference examples. Incidentally, these Examples are not intended to limit the scope of the present invention.

Example 1

Synthesis of 6-(1-fluoroethyl)-4-pyrimidone

To a solution in which 9.33 g of methyl 4-fluoro-3-oxopentanoate had been dissolved in 115 ml of methanol were successively added 36.5 g of a 28% sodium methoxide methanol solution and 9.84 g of formamidine acetate at room temperature, and the mixture was stirred at 40° C. for 12 hours. To the mixture was further added 0.66 g of formamidine acetate and after stirring the mixture at 50° C. for 2 hours, the mixture was cooled to 10° C. or lower. After cooling, a mixture of 9.51 g of conc. sulfuric acid and 8.5 g of water was added to the reaction mixture. After stirring the mixture at 50° C. for 30 minutes, insolubles were removed by filtration and the filtrate was quantitated by the liquid chromatography internal standard method. As a result, 7.99 g of 6-(1-fluoroethyl)-4-pyrimidone was found to be formed (yield: 89.2%). The filtrate was concentrated under reduced pressure and the concentrated solution was recrystallized from 40 ml of 2-propanol to obtain 5.82 g of 6-(1-fluoroethyl)-4-pyrimidone.

Melting point 170 to 171.5° C.

Mass analysis value CI-MS m/e=143 (m+1)

$^1$H-NMR (CDCl$_3$) d (ppm) 1.60 to 1.67 (3H, dd), 5.34 to 5.47 (1H, dq), 6.62 to 6.63 (1H, t), 8.13 (1H, s), 13.3 (1H, bs)

Example 2

Synthesis of 6-(1-fluoroethyl)-4-pyrimidone

To a solution in which 24.3 g of ethyl 4-fluoro-3-oxopentanoate had been dissolved in 330 ml of methanol were added 72.3 g of a 28 % sodium methoxide methanol solution and 15.6 g of formarnidine acetate, and the mixture was stirred at 50° C. for 3 hours. To the mixture was further added 7.81 g of formamidine acetate and after stirring the mixture at 50° C. for 4 hours, the mixture was cooled to 10° C. or lower. After cooling, 18.8 g of conc. sulfuric acid and 13.5 g of water were added to the reaction mixture. After stirring the mixture at 50° C. for 15 minutes, insolubles were removed by filtration and the filtrate was quantitated by the liquid chromatography internal standard method. As a result, 18.0 g of 6-(1-fluoroethyl)-4-pyrimidone was formed (yield: 84.6%).

Example 3

Synthesis of 6-(1-fluoroethyl)-4-pyrimidone

To a solution in which 1.90 g of butyl 4-fluoro-3-oxopentanoate had been dissolved in 5 ml of methanol were added 4.82 g of a 28% sodium methoxide methanol solution and 2.0 g of formamidine acetate, and the mixture was stirred at 50° C. for 7 hours. After completion of the reaction, the reaction mixture was cooled to 10° C. or lower, and quantitated by the liquid chromatography internal standard method. As a result, 1.15 g of 6-(1-fluoroethyl)-4-pyrimidone was found to be formed (yield: 80.9%).

Example 4

Synthesis of 6-(1-fluoro-1-methylethyl)-4-pyrimidone

To a solution in which 5.52 g of ethyl 4-fluoro-4-methyl-3-oxopentanoate had been dissolved in 20 ml of methanol were added 11.6 g of a 28 % sodium methoxide methanol solution and 4.0 g of formamidine acetate, and the mixture was stirred at 50° C. for 6 hours. The mixture was cooled to 10° C. or lower, and 7.1 g of conc. hydrochloric acid was added to the reaction mixture and the reaction mixture was concentrated under reduced pressure. To the concentrated solution was added 100 ml of acetone, and the resulting mixture was stirred at 60° C. for 30 minutes and then, insolubles were removed by filtration. The filtrate was concentrated under reduced pressure and the concentrated solution was recrystallized from 20 ml of acetone to obtain 2.0 g of 6-(1-fluoro-1-methylethyl)-4-pyrimidone (isolated yield: 64.0%).

Melting point 177 to 179° C.

Mass analysis value CI-MS m/e=157 (m+1)

$^1$H-NMR (CDCl$_3$) d (ppm) 1.55 (6H, d), 6.30 (1H, t), 8.20 (1H, s), 12.1 (1H, bs)

Example 5

Synthesis of 6-(1-fluoropentyl)-4-pyrimidone

To a solution in which 3.80 g of ethyl 4-fluoro-3-oxooctanoate had been dissolved in 10 ml of methanol were added 8.97 g of a 28% sodium methoxide methanol solution and 3.72 g of formamidine acetate, and the mixture was stirred at 60° C. for 5 hours. Then, the reaction mixture was concentrated under reduced pressure. To the concentrated solution were added 30 ml of water and 5.0 g of conc. hydrochloric acid, followed by cooling the mixture to 10 C, and the precipitated crystals were separated by filtration. These crystals were recrystallized from 20 ml of 2-propanol to obtain 2.30 g of 6-(1-fluoropentyl)-4-pyrimidone (isolated yield: 67.1%).

Melting point 147.5 to 148.5° C.

Mass analysis value CL-MS m/e=185 (m+1)

$^1$H-NMR (CDCl$_3$) d (ppm) 0.87 (3H, t), 1.25 to 1.40 (4H, m), 1.70 to 2.00 (2H, m), 5.18 to 5.40 (1H, m), 6.29 (1H, t), 8.19 (1H, s), 12.6 (1H, bs)

Example 6

Synthesis of 6-(1-fluoroethyl)-5-methyl-4-pyrimidone

To a solution in which 2.09 g of ethyl 4-fluoro-2-methyl-3-oxopentanoate had been dissolved in 20 ml of methanol were added 4.59 g of a 28 % sodium methoxide methanol solution and 1.61 g of formamidine acetate, and the mixture was stirred under reflux (64° C.) for 3 hours. Then, the reaction mixture was cooled to 10° C. or lower, 2.5 g of conc. hydrochloric acid was added to the mixture and the resulting mixture was concentrated under reduced pressure. To the concentrated solution was added 50 ml of acetone, and the mixture was stirred at 60° C. for 10 minutes, and then insolubles were removed by filtration. The filtrate was concentrated under reduced pressure, and the concentrated solution was recrystallized from 10 ml of acetone to obtain 1.10 g of 6-(1-fluoroethyl)-5-methyl-4-pyrimidone (isolated yield: 59.2%).

Melting point 108 to 109° C.

Mass analysis value CI-MS m/e=157 (m+1)

$^1$H-NMR (CDCl$_3$) d (ppm) 1.46 to 1.58 (3H, dd), 2.00 (3H, d), 5.63 to 5.88 (1H, dq), 8.08 (1H, s), 11.8 (1H, bs)

Reference Example 1

Synthesis of methyl 4-fluoro-3-oxopentanoate

To a liquid in which 1.31 g of a 62.8% sodium hydride had been suspended in 10 ml of tetrahydrofaran was added dropwise a mixed solution of 2.00 g of methyl 2-fluoropropionate and 2.10 g of methyl acetate over 10 minutes, and the mixture was then heated at 30 to 35° C. for 4 hours. After completion of the reaction, the reaction mixture was cooled to room temperature, neutralized with 1N-hydrochloric acid, and subjected to liquid separation. When the organic layer was quantitated by the gas chromatography internal standard method. As a result, it was found that 2.57 g of methyl 4-fluoro-3-oxopentanoate was formed (yield: 92%). When this organic layer was concentrated under reduced pressure and then distilled under reduced pressure, 2.03 g of methyl 4-fluoro-3-oxopentanoate could be obtained.

Boiling point 80 to 81° C./24 to 25 mmHg

Mass analysis value CI-MS m/e=149 (m+1)

$^1$H-NMR (CDCl$_3$) d (ppm) 1.47 to 1.60 (3H, m), 3.66 to 3.67 (1.7H, d), 3.76 to 3.77 (3H, d), 4.87 to 5.12 (1H, m), 5.33 (0.15H, s), 11.80 to 12.00 (0.15H, bs) According to $^1$H-NMR analysis, there is a keto-enol form.

Example 7

Synthesis of 5-chloro-6-(1-fluoroethyl)-4-pyrimidone

A liquid in which 16.0 g of 6-(1-fluoroethyl)-4-pyrimidone had been suspended in 160 ml of dichloroethane was heated to 60° C. and 8.76 g of chlorine was blown thereinto over 20 minutes, and the mixture was further stirred at 60° C. for one hour.

The reaction mixture was cooled to 5° C., and the precipitated crystals were collected by filtration to obtain 25.6 g of crude crystals. When the resulting materials were quantitated by the liquid chromatography internal standard method, it was confirmed that 17.6 g of 5-chloro-6-(1-fluoroethyl)-4-pyrimidone was contained (yield: 88.6%).

This crude crystals were washed with 70 ml of water, and recrystallized from 70 ml of isopropanol to obtain 15.4 g of pure crystal of 5-chloro-6-(1-fluoroethyl)-4-pyrimidone.

Melting point 190 to 191° C.

Mass analysis value CI-MS m/e=177 (m+1)

$^1$H-NMR (CDCl$_3$) d (ppm) 1.49 to 1.60 (3H, dd), 5.76 to 6.00 (1H, dq), 8.27 (1H, s), 13.15 (1H, bs)

Example 8

Synthesis of 5-chloro-6-(1-fluoro-1-methylethyl)-4-pyrimidone

To a liquor in which 1.64 g of 6-(1-fluoro-1-methylethyl)-4-pyrimidone had been suspended in 15 ml of dichloroethane was added 2.00 g of sulfuryl chloride, and then, the mixture was stirred at 40° C. for 3 hours.

The reaction mixture was cooled to room temperature, and after adding 10 ml of water, the mixture was cooled at 5° C. for 2 hours, and the precipitated crystals were separated by filtration to obtain 1.42 g of 5-chloro-6-(1-fluoro-1-methylethyl)-4-pyrimidone (yield: 71.0 %).

Melting point 168 to 171° C.

Mass analysis value CI-MS m/e=191 (m+1)

$^1$H-NMR (DMSO) d (ppm) 1.68 (6H, d), 8.20 (1H, s), 12.00 (1H, bs)

Example 9

Synthesis of 5-chloro-6-(1-fluoropentyl)-4-pyrimidone

To a liquor in which 1.00 g of 6-(1-fluoropentyl)-4-pyrimidone had been suspended in 10 ml of dichloromethane was added 1.47 g of sulfuryl chloride, and then, the mixture was stirred at 40° C. for 3 hours.

The reaction mixture was concentrated under reduced pressure, and after adding 10 ml of water to the concentrated solution, the resulting mixture was cooled at 5° C. for 2 hours, and the precipitated crystal was separated by filtration to obtain 1.10 g of 5-chloro-6-(1-fluoropentyl)-4-pyrimidone (yield: 92.6 %).

Melting point 157 to 160° C.

Mass analysis value CI-MS m/e=219 (m+1)

$^1$H-NMR (DMSO) d (ppm) 0.87 (3H, t), 1.20 to 1.45 (4H, m), 1.70 to 2.09 (2H, m), 5.57 to 5.85 (1H, dq), 8.26 (1H, s), 13.20 (1H, bs)

Reference Example 2

Synthesis of 4,5-dichloro-6-(1-fluoroethyl) pyrimidine

To a liquor in which 1.00 g of 5-chloro-6-(1-fluoroethyl)-4-pyrimidone had been suspended in 10 ml of 1,2-dichloroethane were added one drop of N,N-dimethylformamide and 0.81 g of thionyl chloride, and the mixture was refluxed for 2 hours.

The reaction mixture was washed with 10 ml of water, and then, the organic layer was quantitated by the liquid chromatography internal standard method. As a result, 1.09 g of 4,5-dichloro-6-(1-fluoroethyl)pyrimidine was found to be formed (yield: 98%).

The organic layer was concentrated under reduced pressure, and distilled under reduced pressure, then, 0.76 g of 4,5-dichloro-6-(1-fluoroethyl)pyrimidine was obtained.

Boiling point 84 to 88° C./5 mmHg

Mass analysis value CI-MS m/e=195 (m+1)

$^1$H-NMR (CDCl$_3$) d (ppm) 1.66 to 1.78 (3h, dd), 5.89 to 6.14 (1H, dq), 8.92 (1H, s)

A novel 6-(1-fluoroalkyl)-4-pyrimidone which is important as a synthetic intermediate of aminopyrimidine derivatives which are useful as insecticides, acaricides, fungicides or nematocides, can be obtained by the processes according to the present invention.

We claim:

1. A 6-(1-fluoroalkyl)-4-pyrimidone represented by the following formula:

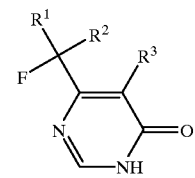

(1)

wherein R$^1$ represents an alkyl group; R$^2$ represents a hydrogen atom or an alkyl group; and R$^3$ represents a hydrogen atom, an alkyl group or a chlorine atom.

2. The 6-(1-fluoroalkyl)-4-pyrimidone according to claim 1, wherein R$^1$ is a straight or branched alkyl group having 1 to 10 carbon atoms, R$^2$ is a hydrogen atom or a straight or branched alkyl group having 1 to 10 carbon atoms, and R$^3$ is a hydrogen atom, a straight or branched alkyl group having 1 to 10 carbon atoms or a chlorine atom.

3. The 6-(1-fluoroalkyl)-4-pyrimidone according to claim 1, wherein $R^1$ is a straight or branched alkyl group having 1 to 4 carbon atoms, $R^2$ is a hydrogen atom or a straight or branched alkyl group having 1 to 4 carbon atoms, and $R^3$ is a hydrogen atom, a straight or branched alkyl group having 1 to 4 carbon atoms or a chlorine atom.

4. The 6-(1-fluoroalkyl)-4-pyrimidone according to claim 1, wherein said compound is selected from the group consisting of:

6-(1-fluoroethyl)-4-pyrimidone,
6-(1-fluoro-1-methylethyl)-4-pyrimidone,
6-(1-fluoropropyl)-4-pyrimidone,
6-(1-fluoro-1-methylpropyl)-4-pyrimidone,
6-(1-fluorobutyl)-4-pyrimidone,
6-(1-fluoro-1-methylbutyl)-4-pyrimidone,
6-(1-fluoropentyl)-4-pyrimidone,
6-(1-fluoro-1-methylpentyl)-4-pyrimidone,
6-(1-fluoroethyl)-5-methyl-4-pyrimidone,
6-(1-fluoro-1-methylethyl)-5-methyl-4-pyrimidone,
6-(1-fluoropropyl)-5-methyl-4-pyrimidone,
6-(1-fluoro-1-methylpropyl)-5-methyl-4-pyrimidone,
6-(1-fluorobutyl)-5-methyl-4-pyrimidone,
6-(1-fluoro-1-methylbutyl)-5-methyl-4-pyrimidone,
6-(1-fluoropentyl)-5-methyl-4-pyrimidone,
6-(1-fluoro-1-methylpentyl)-5-methyl-4-pyrimidone,
5-chloro-6-(1-fluoroethyl)-4-pyrimidone,
5-chloro-6-(1-fluoro-1-methylethyl)-4-pyrimidone,
5-chloro-6-(1-fluoropropyl)-4-pyrimidone,
5-chloro-6-(1-fluoro-1-methylpropyl)-4-pyrimidone,
5-chloro-6-(1-fluorobutyl)-4-pyrimidone,
5-chloro-6-(1-fluoro-1-methylbutyl)-4-pyrimidone,
5-chloro-6-(1-fluoropentyl)-4-pyrimidone, and
5-chloro-6-(1-fluoro-1-methylpentyl)-4-pyrimidone.

5. A process for producing a 6-(1-fluoroalkyl)-4-pyrimidone represented by the following formula (1-A):

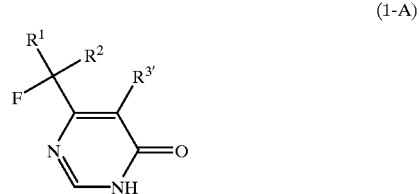

(1-A)

wherein $R^1$ represents an alkyl group; $R^2$ represents a hydrogen atom or an alkyl group; and $R^{3'}$ represents a hydrogen atom or an alkyl group, which comprises allowing a 4-fluoro-3-oxocarboxylate represented by the following formula (2):

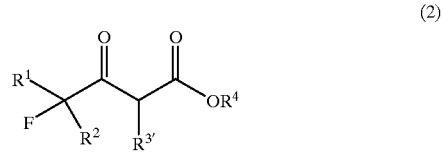

(2)

wherein $R^1$, $R^2$ and $R^{3'}$ have the same meanings as defined above; and $R^4$ represents an alkyl group, to react with formamidine in the presence of a base.

6. The process for producing the 6-(1-fluoroalkyl)-4-pyrimidone according to claim 5, wherein the formamidine is a salt of an acetate, a hydrochloride or a sulfate.

7. The process for producing the 6-(1-fluoroalkyl)-4-pyrimidone according to claim 5, wherein the base is an alkali metal alkoxide.

8. The process for producing the 6-(1-fluoroalkyl)-4-pyrimidone according to claim 5, wherein the base is present in an amount of 1- to 3-fold mol based on the amount of a formamidine salt.

9. A process for producing a 5-chloro-6-(1-fluoroalkyl)-4-pyrimidone represented by the following formula (1-B):

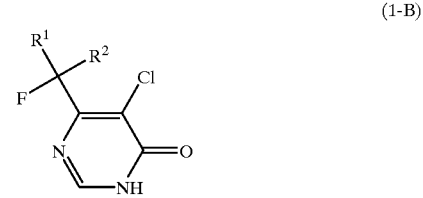

(1-B)

wherein $R^1$ represents an alkyl group; and $R^2$ represents a hydrogen atom or an alkyl group, which comprises subjecting 6-(1-fluoroalkyl)-4-pyrimidone represented by the following formula (1-A'):

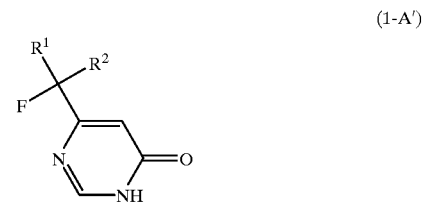

(1-A')

wherein $R^1$ and $R^2$ have the same meanings as defined above, to chlorination reaction with a chlorinating agent.

10. The process for producing the 5-chloro-6-(1-fluoroalkyl)-4-pyrimidone according to claim 9, wherein the chlorinating agent is chlorine or sulfuryl chloride.

11. The process for producing the 5-chloro-6-(1-fluoroalkyl)-4-pyrimidone according to claim 9, wherein the chlorinating agent is used in an amount of 0.9 to 4.0-fold mol based on the amount of the compound (1-A').

12. The process for producing the 5-chloro-6-(1-fluoroalkyl)-4-pyrimidone according to claim 9, wherein the reaction is carried out at −10 to 100° C. for 0.5 to 10 hours.

* * * * *